(12) United States Patent
DiTroia et al.

(10) Patent No.: US 10,624,622 B2
(45) Date of Patent: Apr. 21, 2020

(54) SURGICAL RETRACTION DEVICE

(71) Applicants: Worcester Polytechnic Institute, Worcester, MA (US); University of Massachusetts, Boston, MA (US)

(72) Inventors: Jacquelyne DiTroia, Worcester, MA (US); Caroline Mazzola, Westport, MA (US); Andres Monterroso, Guatemala (GT); Patricia Swierk, Saugus, MA (US); Arriyan Samandar Dowlatshahi, Chestnut Hill, MA (US); Kristen Billiar, Worcester, MA (US); Raymond M. Dunn, Worcester, MA (US)

(73) Assignees: Worcester Polytechnic Institute, Worcester, MA (US); University of Massachusetts, Boston, MA (US)

( * ) Notice: Subject to any disclaimer, the term of this patent is extended or adjusted under 35 U.S.C. 154(b) by 95 days.

(21) Appl. No.: 15/491,107

(22) Filed: Apr. 19, 2017

(65) Prior Publication Data
US 2017/0296159 A1 Oct. 19, 2017

Related U.S. Application Data

(60) Provisional application No. 62/324,595, filed on Apr. 19, 2016.

(51) Int. Cl.
*A61B 17/02* (2006.01)
*A61B 17/00* (2006.01)
*A61B 17/32* (2006.01)

(52) U.S. Cl.
CPC ............ *A61B 17/0206* (2013.01); *A61B 2017/00902* (2013.01); *A61B 2017/320044* (2013.01)

(58) Field of Classification Search
CPC ............................. A61B 17/02–0206
See application file for complete search history.

(56) References Cited

U.S. PATENT DOCUMENTS 2,831,480 A * 4/1958 Milano ............... A61B 1/24
433/93
3,998,217 A 12/1976 Trumbull et al.
(Continued)

FOREIGN PATENT DOCUMENTS

RU 115198 U1 4/2012

OTHER PUBLICATIONS

International Search Report, PCT/US2017/028337, dated Sep. 14, 2017, pp. 2.

*Primary Examiner* — Jacqueline T Johanas
*Assistant Examiner* — Michelle C Eckman
(74) *Attorney, Agent, or Firm* — Armis IP Law, LLC (57) ABSTRACT

A surgical appliance includes a pair of opposed prongs slideably disposed on an elongated locking track for retracting neurovascular and musculotendinous anatomical structures through an incision for affording access to deeper structures for inserting osteosynthesis hardware in the surgical treatment of a distal radius fracture or other surgical procedure. The prongs extend from retractors that traverse the locking track for opposed linear movement while recessed in a surgical working region accessible through an incision. The prongs terminate in curvatures defining a void that gather and engage the elongated anatomical structures on top of the skeletal members receiving the plate. The prongs draw back the tendons, blood vessels and nerve structures to allow unimpeded surgical access for manipulating and attaching skeletal and soft tissue members and/or appliances. The device retracts anatomical structures along (Continued)

a linear track for a fixed locking engagement maintaining a surgical gap without direct manual assistance.

11 Claims, 5 Drawing Sheets

(56) References Cited

U.S. PATENT DOCUMENTS

| | | | | |
|---|---|---|---|---|
| 4,616,633 A * | 10/1986 | Vargas Garcia | ....... | A61B 17/02 600/206 |
| 5,512,038 A * | 4/1996 | O'Neal | ............. | A61B 17/0206 600/210 |
| 5,616,117 A * | 4/1997 | Dinkler | ............. | A61B 17/0206 600/210 |
| 5,902,233 A | 5/1999 | Farley et al. | | |
| 5,964,697 A * | 10/1999 | Fowler, Jr. | ......... | A61B 17/0293 600/210 |
| 6,102,854 A * | 8/2000 | Cartier | .................... | A61B 1/32 600/210 |
| 6,409,731 B1 * | 6/2002 | Masson | ................. | A61B 17/02 600/210 |
| 6,458,079 B1 * | 10/2002 | Cohn | ..................... | A61B 17/02 600/210 |
| 6,500,116 B1 * | 12/2002 | Knapp | ............... | A61B 17/0206 600/210 |
| 6,997,872 B1 * | 2/2006 | Bohanan | ................ | A61B 17/02 600/210 |
| 7,018,332 B1 * | 3/2006 | Masson | ................. | A61B 17/02 600/201 |
| 7,232,411 B2 * | 6/2007 | Dinkler, II | ............. | A61B 17/02 600/230 |
| 8,900,137 B1 * | 12/2014 | Lovell | ................... | A61B 17/02 600/210 |
| 8,945,003 B2 * | 2/2015 | Bass | .................. | A61B 17/0206 600/214 |
| 9,113,853 B1 * | 8/2015 | Casey | ................ | A61B 17/0206 |
| 9,289,199 B1 * | 3/2016 | Sami | ................ | A61B 17/0231 |
| 9,795,370 B2 * | 10/2017 | O'Connell | ......... | A61B 17/0206 |
| 9,999,414 B2 * | 6/2018 | Ruppert | ............ | A61B 17/0206 |
| 10,149,674 B2 * | 12/2018 | Angus | ................. | A61B 17/025 |
| 2004/0092797 A1 * | 5/2004 | Yi | .......................... | A61B 17/02 600/210 |
| 2005/0177028 A1 * | 8/2005 | Royce | ............... | A61B 17/0206 600/210 |
| 2005/0192484 A1 * | 9/2005 | Sharratt | ................ | A61B 17/02 600/210 |
| 2006/0189848 A1 * | 8/2006 | Penenberg | ............... | A61B 1/32 600/210 |
| 2007/0055110 A1 * | 3/2007 | Bass | ...................... | A61B 17/02 600/234 |
| 2007/0179345 A1 * | 8/2007 | Santilli | ............. | A61B 17/0206 600/227 |
| 2008/0294011 A1 * | 11/2008 | McLoughlin | .......... | A61B 17/02 600/210 |
| 2009/0076516 A1 * | 3/2009 | Lowry | .................. | A61B 17/02 606/90 |
| 2009/0192360 A1 * | 7/2009 | Riess | ..................... | A61B 17/02 600/210 |
| 2010/0113885 A1 * | 5/2010 | McBride | ................. | A61B 1/32 600/224 |
| 2010/0256454 A1 * | 10/2010 | Farley | .................... | A61B 17/02 600/210 |
| 2010/0268036 A1 * | 10/2010 | Rothweiler | ........ | A61B 17/0206 600/214 |
| 2011/0184245 A1 * | 7/2011 | Xia | .................... | A61B 17/0206 600/202 |
| 2011/0270042 A1 * | 11/2011 | Giulianotti | ............. | A61B 17/02 600/228 |
| 2012/0088979 A1 * | 4/2012 | Nunley | ................ | A61B 17/025 600/231 |
| 2012/0265021 A1 * | 10/2012 | Nottmeier | ............ | A61B 1/3135 600/219 |
| 2012/0316401 A1 * | 12/2012 | Matsumura | ........ | A61B 17/0206 600/235 |
| 2012/0330106 A1 * | 12/2012 | Wright | ............... | A61B 17/0206 600/218 |
| 2013/0046147 A1 * | 2/2013 | Nichter | .................... | A61B 1/32 600/228 |
| 2013/0237769 A1 * | 9/2013 | Puskas | ..................... | A61B 1/32 600/232 |
| 2013/0245383 A1 * | 9/2013 | Friedrich | ............... | A61B 17/02 600/228 |
| 2013/0245384 A1 * | 9/2013 | Friedrich | ................ | A61B 17/02 600/230 |
| 2014/0066718 A1 * | 3/2014 | Fiechter | ............ | A61B 17/0206 600/214 |
| 2015/0018624 A1 * | 1/2015 | Beck | ........................ | A61B 1/32 600/206 |
| 2015/0250467 A1 * | 9/2015 | Higgins | ............. | A61B 17/0206 600/215 |
| 2015/0354751 A1 * | 12/2015 | Slagle | .................... | A61B 90/50 248/316.1 |
| 2015/0359527 A1 * | 12/2015 | Cao | ........................ | A61B 17/02 600/210 |
| 2016/0213365 A1 * | 7/2016 | Vogtherr | ............ | A61B 17/0206 |
| 2016/0287234 A1 * | 10/2016 | Bass | ................. | A61B 17/02 |
| 2017/0095241 A1 * | 4/2017 | Perler | .................... | A61B 90/30 |
| 2017/0100116 A1 * | 4/2017 | Erramilli | ............. | A61B 17/7035 |
| 2017/0224322 A1 * | 8/2017 | Puskas | ............... | A61B 17/0206 |
| 2017/0296159 A1 * | 10/2017 | DiTroia | ............. | A61B 17/0206 |
| 2017/0311940 A1 * | 11/2017 | Daavettila | .......... | A61B 17/0206 |
| 2017/0311941 A1 * | 11/2017 | Daavettila | .......... | A61B 17/0206 |
| 2018/0168566 A1 * | 6/2018 | O'Connell | ........... | A61B 17/025 |
| 2018/0249992 A1 * | 9/2018 | Truckey | ............. | A61B 17/025 |
| 2018/0353059 A1 * | 12/2018 | Tesar | .................... | A61B 17/02 |
| 2018/0353165 A1 * | 12/2018 | Friedrich | ............... | A61B 17/02 |
| 2019/0008498 A1 * | 1/2019 | McClymont | ......... | A61B 17/025 |
| 2019/0015089 A1 * | 1/2019 | Rosenbaum | ....... | A61B 17/0206 |
| 2019/0021715 A1 * | 1/2019 | O'Connell | ............ | A61B 17/025 |

\* cited by examiner

SURGICAL RETRACTION DEVICE

RELATED APPLICATIONS

This application claims the benefit under 35 U.S.C. § 119(e) of U.S. Provisional Patent Application No. 62/324,595 filed Apr. 29, 2016, entitled "TISSUE RETRACTOR FOR RADIUS FRACTURES," incorporated herein by reference in entirety.

BACKGROUND

A distal radius fracture is one of the more common hand and wrist surgeries performed. Treatment often requires attachment of a surgical implant to bone structures for adding strength. The surgical procedure for addressing this type of fracture can be complicated due to the number and proximity of adjacent structures, such as muscles, ligaments, tendons, and blood vessels that surround this area. The corresponding procedure requires that the tissues and muscles in the wrist be moved so that the bone can be exposed. Various surgical retraction tools are available to manipulate tissues and anatomical structures during surgery. Conventional retractors include manual articulated or rigid elongation members for positioning the adjacent anatomy by manual operation by a surgeon or assistant.

SUMMARY

A surgical appliance includes a pair of opposed prongs slideably disposed on an elongated locking track for retracting neurovascular and musculotendinous anatomical structures through an incision for affording access to a skeletal structure for attaching a plate or support member in treatment of a distal radius fracture surgery or other surgical procedure. The prongs extend from retractors that traverse the locking track for opposed linear movement while recessed in a surgical working region accessible through the incision. The prongs terminate in curvatures defining a void that gather and engage the elongated anatomical structures on above the skeletal members receiving the plate. The prongs draw back the tendons, blood vessels and nerve structures to allow unimpeded access for attaching the plate to a bone element.

Configurations herein are based, in part, on the observation that surgical procedures often employ tools for disposing, securing and maintaining anatomical structures in particular positions to permit surgical access. Such tools, or retractors, may often take the form of a scissors arrangement of pivoting members, or a single elongated member for applying leveraged force. Unfortunately, conventional approaches to surgical tool design suffer from the shortcoming that conventional surgical retraction devices often require active operation by a surgeon or assistant to physically dispose the retractor at the surgical site and maintain a retracted position. While some conventional devices have ratcheting mechanisms for maintaining an "open" position, these devices often travel in an arcuate path, tending to slip out or disengage from misaligned opposed forces. Further, a ratcheting closure affords movement only in increments defined by a granularity or spacing of the ratchet teeth. Accordingly, configurations disclosed herein substantially overcome the above-described shortcoming of conventional surgical tools by providing a locking, linear based retraction device for fixing an extremity in a pronate position while retracting tendons, vessels and nerves alongside a bone or skeletal member for implanting a plate or skeletal support device.

In operation, the method of retracting anatomical structures from a surgical working region (also called "surgical field") using the disclosed surgical retraction device for retracting tissue includes disposing a prong of a first retractor into an incision, in which the retractor is slideably attached to an elongated track. The retractor is also opposed to a second retractor on the elongated track, and a prong of the second retractor is disposed against an opposed side of the incision from the first retractor. Upon insertion, a curvature at a distal end of each prong inserted in the incision engages elongated anatomical structures such as tendons, flood vessels and nerves that lie between the incision and a skeletal member upon which a surgical plate is to be attached. The first and second retractors are disposed in opposed linear directions on the elongated track for drawing the elongated anatomical structures to opposed sides to define a gap for providing surgical access to the skeletal member, and a track lock secures the first and second retractors in the opposed positions defining the gap.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Configurations below depict an example implementation of the surgical retraction tool employed for implantation of a plate on the radius for repair of a distal radius fracture involving the wrist of a patient. Alternative uses include use of the surgical retraction tool on other extremities and surgical regions for retraction along a linear track for a fixed locking engagement and maintaining a surgical field without direct manual assistance.

Distal radius fractures are one of the more common fractures seen by hand surgeons. The standard surgical approach to the distal radius is the volar approach which involves making an incision on the volar aspect (the palm side) of the forearm at the wrist level. This allows for a safe and extensile exposure of the fractured aspect of the distal radius, allowing for reduction of the fracture and placement of hardware to retain the fracture in its correct or reduced position. Most commonly this involves using a plate and screws. The challenge here is that there are numerous structures that run longitudinally down the arm into the hand, and traverse the surgical field. These need to be retracted and protected in order for the procedure to be performed safely and efficiently. There are two types of surgical retractors: handheld devices which require surgeon or assistant to hold in one hand, and self-retaining retractors which do not need to be held in position manually, once they are inserted into the wound. The currently available self-retaining retractors have numerous shortcomings, hence the novel design described herein.

Figure 1:
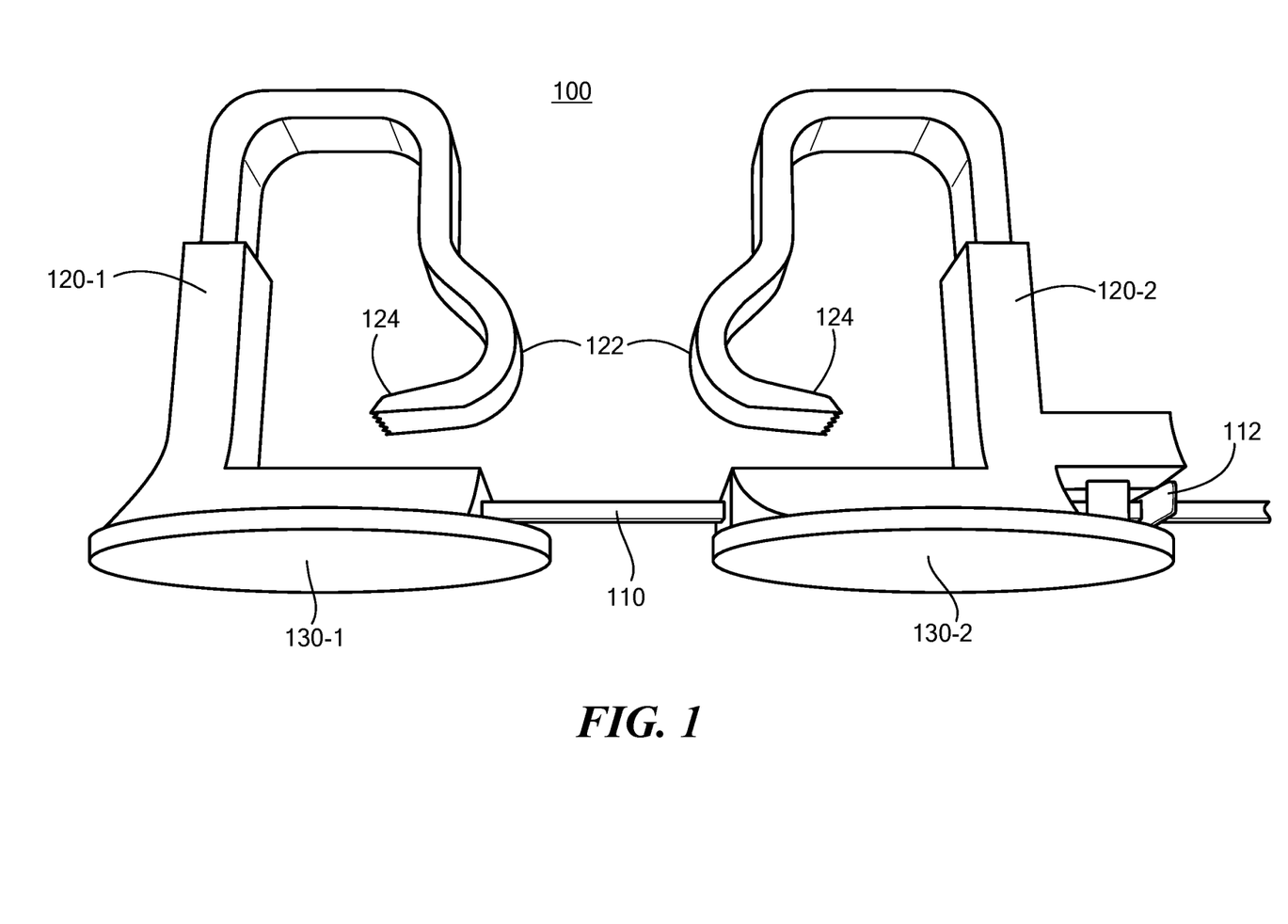
FIG. 1 is a perspective view of the surgical retraction device for use as disclosed herein.

FIG. 1 is a perspective view of the surgical retraction device for use as disclosed herein. Referring to FIG. 1, the tissue retraction device 100 is operable for retracting tissue over a surgical field defined by an incision in an extremity such as an arm or leg. The retraction device 100 includes an elongated track 110 and opposed, self-retaining retractors 120-1, 120-2 (120 generally) disposed on the track 110, such that at least one of the retractors slideably engages the track 110 for linear positioning along the track 110. Alternatively, both retractors 120 may be moveable, but generally the relative distance between the retractors 120 can be effectively altered by disposing either. Each retractor 120 includes a curvature 122 adapted to engage elongated anatomical structures on opposed sides of the surgical field, and a track lock 112 on the retractor 120 for selectively securing the retractor 120 to the track 110. The track lock 112 is selectively engageable by a spring-loaded lever or button for disposing the retractors 120 in an opposed linear arrangement on the track 110.

In a particular arrangement as depicted, the retractors 120 comprise a radiolucent material adapted for transparency of scanning electromagnetic radiation. The radiolucency of the material allows imaging technology, such as MRI, CT scans, x-ray and other imaging technology to "scan through" the retractors such that the retractors will not appear or interfere with such imaging. Generally, such imaging expects denser tissue structures to reflect, refract, or otherwise augment a directed waveform received by an imaging sensor. The radiolucent construction permits electromagnetic and other imaging radiation to pass through the retractors and allows such scans to be free of interference of retractor images.

In operation, a surgeon disposes the track 110 on the patient's extremity behind the surgical field (on the opposite side of the extremity). In a preferred arrangement, with an upwards facing incision, the track would be beneath the arm or other extremity, thus wrapping around the extremity to be operated on. After engaging the retractors on opposite sides of an incision, the retractors 120 are drawn apart to engage anatomical structures and draw them to respective sides of the incision, leaving a gap in the surgical field for access to the radius or other structure.

In general, the track 110 is intended to support the retractors 120 well away and distal from the surgical field. For an extremity such as an arm or leg, this would be the opposed, or back of the extremity opposed from the incision. In a tabletop orientation, the track would be disposed along the back or bottom of an extremity with an upward facing incision. In general, the track 110 and retractors 120 form a "wrap around" position that exposes the surgical field in an opening between the retractors 120. The track occupies a "back" or opposed region away from the surgical field, and the retractors 120 would occupy flanking or side positions of the retractors 120 around an anatomical area in which the incision is made. Such positioning allows the device, after complete assembly, and in its final resting position, to wrap around the extremity, in effect coming into the surgical field from behind, considering that the surgical field is represents the front of the extremity. The surgical field may be located anywhere on the extremity: medial, lateral, anterior, posterior or a combination of the aforementioned.

The track lock 112 secures the retractor 120 to the track 110 by a biased tension that secures the retractor 120 to the track 110 in a rest position and permits slideable movement responsive to a disengaging force for removing the biased tension. The retractor 120 therefore is locked to the track 110 while in an unattended, hands-free state such that an assistant does not need to crowd the surgical field to tend to or actively hold the device to maintain tissue retraction. Upon engagement, the track lock 112 is disengaged, the retractors 120 separated a suitable distance, and the track lock 110 released to engage the lock and fix the retractor 120 to the track. As indicated above, both retractors may have a lock, but a single lock on either retractor will suffice for separating the retractors 120.

The retractors 120 have a serration 124 at a distal end of the curvature 122. The serration 124 is adapted to engage a resilient tissue such as muscle in the surgical field, in which the curvature 122 is disposed adjacent the serration 124 for gathering abrasion sensitive anatomical structures away from the serration 124. The serration 124 is positioned to engage muscle tissue immediately above the bone, in the case of a distal radius procedure. The muscle tissue is sufficiently resistant to abrasion and puncture such that the serrations will not injure the muscle. The curvature 122, in contrast, is positioned to embrace more sensitive vascular and nerve structures above the muscle, discussed further below in FIG. 5.

Figure 2:
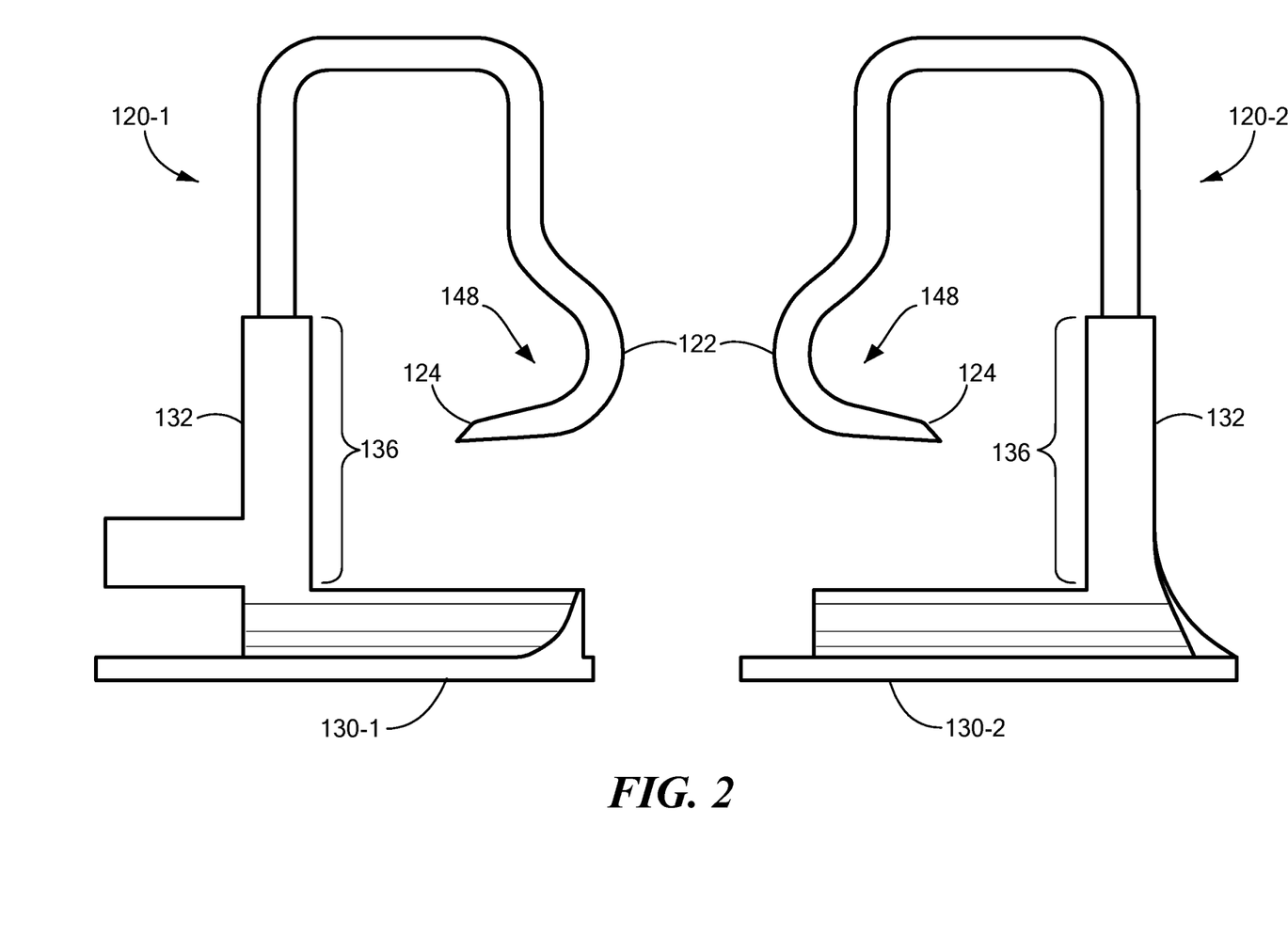
FIG. 2 is a side elevation of the retraction device as in FIG. 1.

FIG. 2 is a side elevation of the retraction device as in FIG. 1. Referring to FIGS. 1 and 2, the device further includes a base 130, such that each retractor 120 is secured to a base 130-1, 130-2 (130 generally). Each the bases 130 is adapted to engage a horizontal planer surface such as a operating table or table extension for maintaining an upward facing orientation of the incision and working surgical field. Just above the base is a shield 130, which may be employed above the track lock 110 to avoid accidental disengagement.

Figure 3:
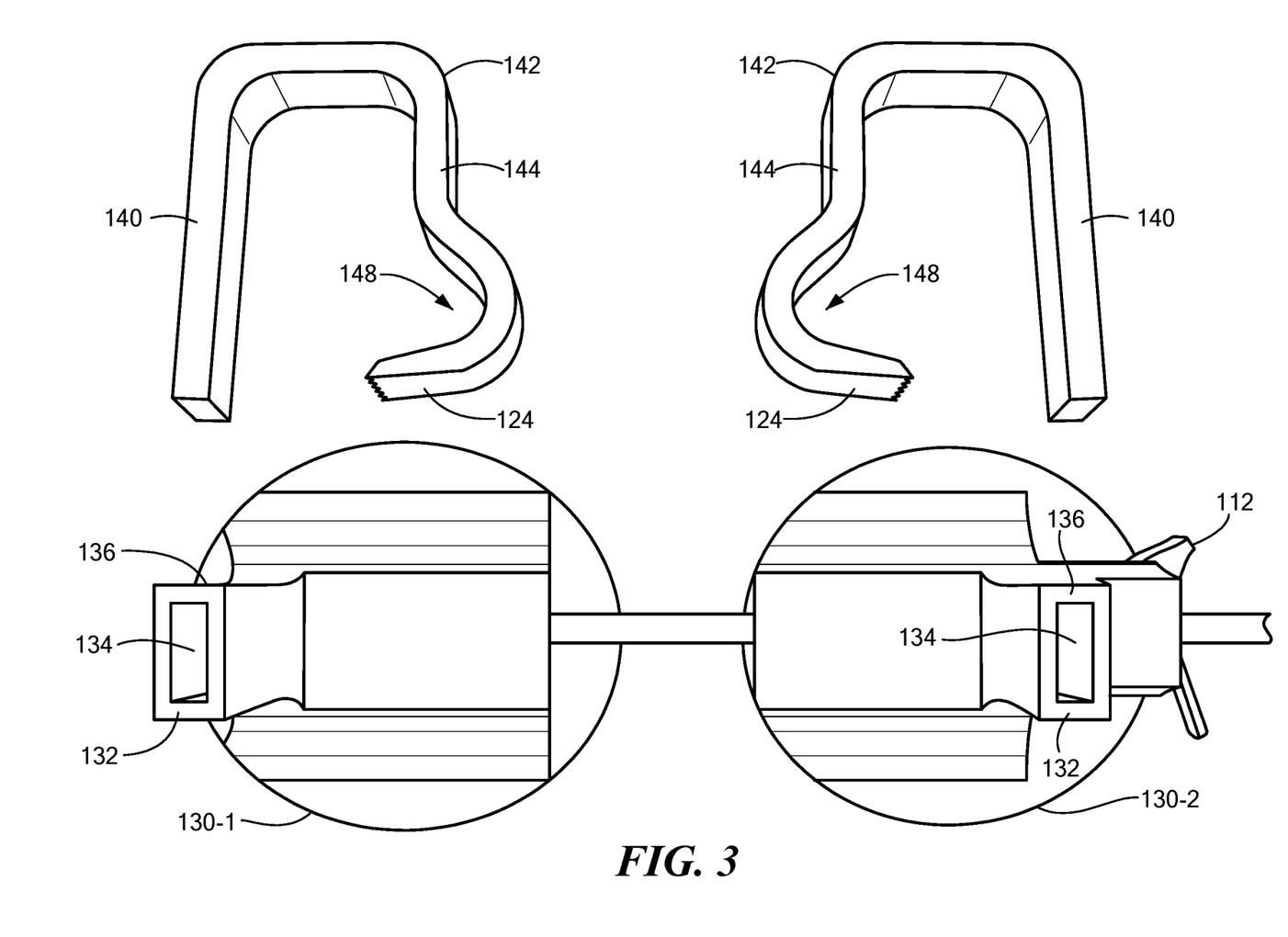
FIG. 3 is a disassembled view of the retraction device as in FIG. 1.

FIG. 3 is a disassembled view of the retraction device as in FIG. 1. Referring to FIGS. 1-3, each of the retractors 120 further includes a post 140, a transverse 142, and a prong 144. The base 130 further comprises a tower 132 having a recess 134 adapted to receive the post 140, and a depth 136 for defining an insertion distance, such that the post 140 is operable for engagement with the respective tower 132 for defining a distance from the base 130 to the transverse 142 for varying an insertion depth of the prong into the surgical field. The post 140 therefore extends into a tower 134 attached to the base 130 for setting a depth 136 of insertion of the prong 144 into the incision. Generally, the end of the prong 144 is such that the serration 124 engages muscle tissue just above the bone (radius).

Continuing to refer to FIGS. 1-3, the transverse 142 extends substantially perpendicularly from the post 140 and is adapted to extend in a direction over the surgical field. The prong 144 is substantially perpendicular to the transverse 142 and parallel to the post 140, such that the prong is adapted to extend into the surgical field beyond imposing surgical structures. Upon insertion, each opposed transverse 142 from the respective retractors 120 will almost meet, as the prongs are inserted into the incision to begin drawing the incision apart. The curvature 122 is formed at a distal end of the prong 144 and defines a void 148 for gathering elongated anatomical structures, such as blood vessels, nerves, connective tissue, and any other neurovascular and musculotendinous structures otherwise obscuring the installation of the surgical plate.

As indicated above, during device installation after forming the incision, a fixed retractor 120 and a sliding retractor 120 are positioned, such that the fixed retractor is secured at an end of the track 110, and the sliding retractor has the track lock 112 for slideably disposing the retractor 120 and varying a total distance between the retractors based on liner movement along the track 110. The track lock 110 may frictionally engage the base 130 to the elongated track 110 by biasing a frictional body against the track under the spring load of the track lock 112. Alternative, any suitable fixation such as a ratchet, dimple, rolling gear and tooth arrangement may suffice.

Figure 4:
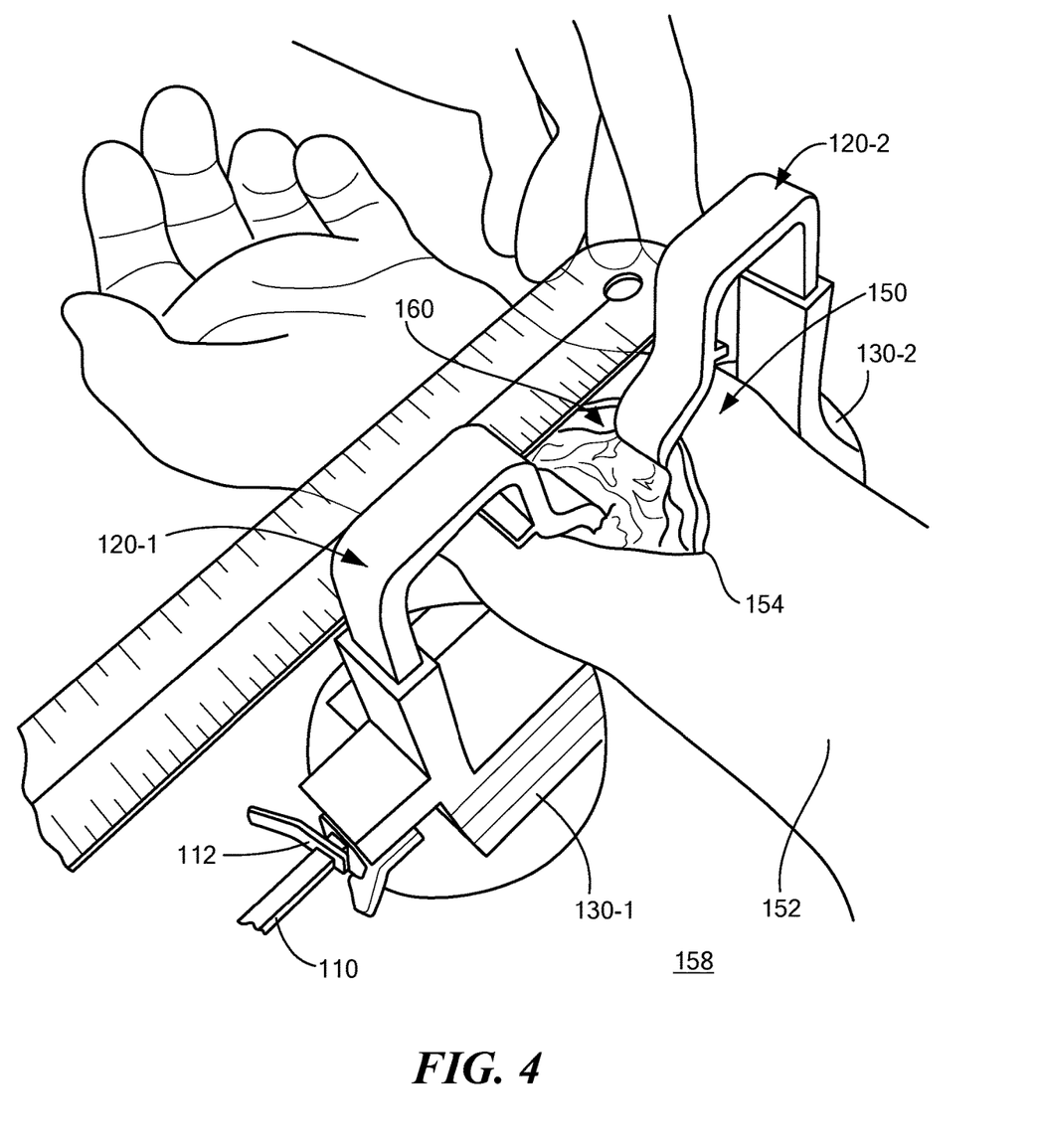
FIG. 4 shows the retraction device of FIG. 1-3 installed in a surgical field.

FIG. 4 shows the retraction device of FIG. 1-3 installed in a surgical field 160. Referring to FIG. 4, the elongated track 110 is adapted to be disposed on a distal side of an extremity 152 opposed from the incision 154 defining the surgical field 160 defined by retracted anatomical structures 150. FIG. 4 shows that the base 130 is adapted to secure the retractors 120 for maintaining a pronate position of a surgical extremity 152 defining the surgical field 160, such that the pronate position disposes the incision 154 in an upward facing manner on a horizontal surface 158. While a pronate position may be preferred by many surgeons, the surgical device 100 could also be disposed around other suitable extremities or anatomical regions. Since the biasing force of the retracted anatomical structures fixes the surgical device 100 in the locked, open position, surgical incisions 154 on other anatomical regions may be performed, and the bases either omitted or allowed other orientation.

Figure 5:
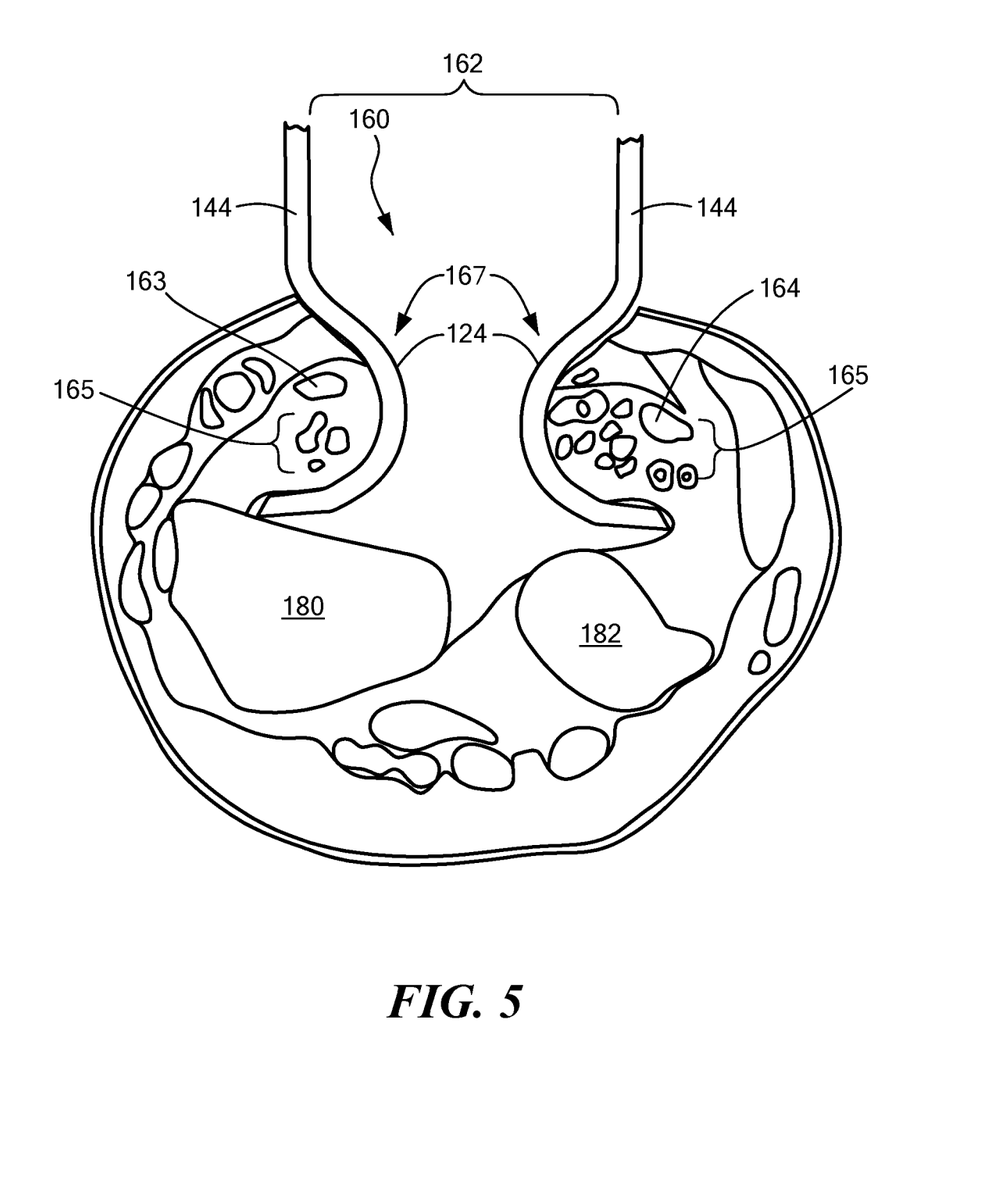
FIG. 5 shows a side cutaway view of anatomical structures retracted by the device of FIG. 1 in the surgical field.

FIG. 5 shows a side cutaway view of anatomical structures retracted by the device of FIG. 1 in the surgical field 160. In the surgical field 160, the opposed retractors 120 define a gap 162. The resulting gap 162 is closeable and expandable by disposing the retractors 120 in a linear manner along the track 110, such that the surgical field 160 increasingly accessible with an expanding gap 162. The gap 162 is formed from gathering and retraction of anatomical structures in the void 148 defined by the curvature 122. Neurovascular and musculotendinous structures are concentrated above the radius 180 and ulna 182 in the surgical field 160, and include the radial nerve 163, ulnar nerve 164, and other elongated anatomical structures 165 such as tendons, ligaments, and blood vessels. Of particular note is the prong 144 having a depth 136 and a connection 167 to the transverse 142, forming a corner or recess such that the connection 167 is adapted to retain a nerve structure based on the depth from the connection 167 to a surface of a bone (radius 180 or ulna 182) in the surgical field. The insertion depth of the prong 144 based on the tower depth 136 affords the ulnar nerve a secure position adjacent the connection that is well above the surgical attachment activities occurring on the radius 180 for plate installation.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A surgical retraction device for retracting tissue over a surgical field defined by an incision, comprising:
    an elongated track adapted to be disposed in an opposed region of an anatomical area from the incision defining the surgical field;
    opposed, self-retaining retractors disposed on the elongated track, at least one of the retractors slideably engaging the elongated track for linear positioning along the elongated track, the opposed retractors defining a gap, the gap closeable and expandable by disposing the opposed retractors in a linear manner along the elongated track, the surgical field increasingly accessible with an expanding gap;
    a curvature on each retractor of the retractors, each curvature adapted to engage elongated anatomical structures on opposed sides of the surgical field;
    a track lock on at least one retractor of the retractors for selectively securing the at least one retractor to the elongated track, the track lock selectively engageable for disposing the retractors in an opposed linear arrangement; and
    a base secured to each retractor, the bases adapted to engage a planer surface for maintaining an upward facing orientation of the incision and surgical field;
    each base further comprising a tower, each tower having a recess adapted to receive the respective retractor, and a depth for defining an insertion distance, each retractor operable for engagement with the tower for defining a distance from the respective base to transverse for varying an insertion depth into the surgical field.

2. The device of claim 1, wherein the track lock biases a frictional body against the track.

3. The device of claim 1, wherein the track lock secures the at least one retractor to the track by a biased tension, the biased tension securing the at least one retractor to the track in a rest position and permitting slideable movement responsive to a disengaging force for removing the biased tension.

4. The device of claim 3, wherein the retractors comprise a fixed retractor and a sliding retractor, the fixed retractor secured at an end of the elongated track, the sliding retractor having the track lock for slideably disposing the sliding retractor for varying a total distance between the retractors based on liner movement along the elongated track.

5. The device of claim 1, wherein each retractor further includes a post, transverse, and a prong;
    each post extending into the respective tower attached to the respective base;
    each transverse extending substantially perpendicularly from the respective post and adapted to extend in a direction over the surgical field;
    each prong substantially perpendicular to the respective transverse and parallel to the respective post, each prong adapted to extend into the surgical field beyond imposing surgical structures; and
    each curvature disposed at a distal end of the respective prong and defining a void for gathering neurovascular and musculotendinous structures defining the elongated anatomical structures.

6. The device of claim 5, further comprising a serration at a distal end of the respective prongs, each serration adapted to engage a resilient tissue in the surgical field, each curvature disposed adjacent the respective serration for gathering abrasion sensitive anatomical structures away from the respective serration.

7. The device of claim 5, wherein each base is adapted to secure the retractors for maintaining the position of a operated extremity defining the surgical field, ensuring the incision is facing upwards and in clear line of sight.

8. The device of claim 1, wherein the retractors comprise a radiolucent material adapted for transparency of scanning electromagnetic radiation.

9. The device of claim 1, wherein the track lock is adapted to bias a frictional body against the elongated track under a spring load.

10. The device of claim 1, wherein the retractors and the respective curvatures extend from the elongated track in a direction parallel to a plane defined by the retractors and the elongated track.

11. A surgical retraction device for retracting tissue over a surgical field defined by an incision, comprising:
- an elongated track adapted to be disposed in an opposed region of an anatomical area from the incision defining the surgical field;
- opposed, self-retaining retractors disposed on the elongated track, at least one of the retractors slideably engaging the track for linear positioning along the elongated track;
- a curvature on each retractor of the retractors, each curvature adapted to engage elongated anatomical structures on opposed sides of the surgical field; and
- a track lock on the at least one retractor for selectively securing the at least one retractor to the track, the track lock selectively engageable for disposing the retractors in an opposed linear arrangement;
- each retractor further including a post, a transverse, and a prong;
  - each post extending into a tower attached to a base;
  - each transverse extending substantially perpendicularly from the respective post and adapted to extend in a direction over the surgical field;
  - each prong substantially perpendicular to the transverse and parallel to the respective post, each prong adapted to extend into the surgical field beyond imposing surgical structures; and
  - each curvature disposed at a distal end of the respective prong and defining a void for gathering neurovascular and musculotendinous structures defining the elongated anatomical structures,
- each prong having a depth and a respective connection to the respective transverse, the respective connection adapted to retain a nerve structure based on the depth from the respective connection to a surface of a bone in the surgical field.

* * * * *